United States Patent
Matsumoto et al.

(10) Patent No.: US 7,490,744 B2
(45) Date of Patent: Feb. 17, 2009

(54) BACKFLOW PREVENTING MOUTH PLUG AND CONTAINER

(75) Inventors: Koichi Matsumoto, Kobe (JP); Masayasu Miyazaki, Yokohama (JP)

(73) Assignee: Sumitomo Rubber Industries, Ltd., Kobe-Shi, Hyogo (JP)

( * ) Notice: Subject to any disclaimer, the term of this patent is extended or adjusted under 35 U.S.C. 154(b) by 416 days.

(21) Appl. No.: 11/024,776

(22) Filed: Dec. 30, 2004

(65) Prior Publication Data

US 2005/0173468 A1    Aug. 11, 2005

(30) Foreign Application Priority Data

Feb. 5, 2004   (JP)   ............... 2004-029826
Apr. 16, 2004  (JP)   ............... 2004-122149

(51) Int. Cl.
    B65D 47/20    (2006.01)
(52) U.S. Cl. .................. 222/494; 222/207; 222/213; 222/422
(58) Field of Classification Search .......... 222/206, 222/207, 212, 213, 420, 422, 490, 491, 494
    See application file for complete search history.

(56) References Cited

U.S. PATENT DOCUMENTS 2,209,665 A * 7/1940 Scheringer ............. 222/494
3,111,703 A * 11/1963 Kaufman ................ 401/214
3,179,300 A * 4/1965 Davidson et al. ........... 222/213
4,863,071 A * 9/1989 Guss et al. ............... 222/207
2006/0065673 A1* 3/2006 Miyazaki et al. .......... 222/96

FOREIGN PATENT DOCUMENTS

| JP | 52-91354 A | 8/1977 |
| JP | 63-98776 A | 4/1988 |
| JP | 1-128875 A | 5/1989 |
| JP | 2002-39409 A | 2/2002 |
| JP | 2003-126218 A | 5/2003 |
| WO | WO 2004/022444 A1 | 3/2004 |

* cited by examiner

Primary Examiner—J. Casimer Jacyna
(74) Attorney, Agent, or Firm—Birch, Stewart, Kolasch & Birch, LLP

(57) ABSTRACT

There is provided a backflow preventing mouth plug comprising an elastic membrane element having a discharge opening for discharging fluid and mounted to a mouth part of a container and a plug member disposed in the elastic membrane element to prevent unintentional outflow of the fluid. The plug member has a spherical seal surface with which the elastic membrane element elastically and closely contacts. At least one thick wall portion and at least one thin wall portion are alternately formed around the discharge opening of the elastic membrane element in a circumferential direction thereof.

15 Claims, 8 Drawing Sheets

BACKFLOW PREVENTING MOUTH PLUG AND CONTAINER

BACKGROUND OF THE INVENTION

1. Field of the Invention

The present invention relates to a backflow preventing mouth plug mounted to a mouth part of a container body, and to a container comprising the backflow preventing mouth plug.

2. Description of the Related Art

A conventional backflow preventing mouth plug is disclosed in Japanese Patent Laid-Open No. 2002-39409. The backflow preventing mouth plug includes a spherical valve and a plug body for receiving the spherical valve. The spherical valve is received in a spherical valve receiving part defined in the plug body. In the backflow preventing mouth cap, a lower sealing portion which contacts the spherical valve to perform a sealing function and an upper sealing portion which seals the spherical valve above the lower sealing portion are formed in the spherical valve receiving part. In using the backflow preventing mouth cap, the spherical valve can be moved between the lower and upper sealing portions.

In the conventional backflow preventing mouth cap, since the spherical valve can be moved in the spherical value receiving part, when the spherical valve is brought into contact with the lower sealing portion to be sealed, a void is created above the spherical valve and fluid may remain in the void. Because this remaining fluid is exposed to oxygen or to saprophytic bacteria that is commonly present in air, the remaining fluid is likely to be oxidized by oxygen or be contaminated by the saprophytic bacteria. Also, due to the fact that no sealing portion is provided while the spherical valve is moved from the upper sealing portion to the lower sealing portion, outside air or saprophytic bacteria may also enter the container.

SUMMARY OF THE INVENTION

The invention is made to solve the above problems, and it is an object of the invention to provide a backflow preventing mouth plug that prevents a void from being created therein and contents from remaining in the void.

Another object of the invention is to provide a container having the backflow preventing mouth plug that prevents a void from being created therein and contents from remaining in the void.

In order to achieve the above objects, according to one aspect of the invention, there is provided a backflow preventing mouth plug comprising an elastic membrane element having a discharge opening for discharging fluid and mounted to a mouth part of a container and a plug member disposed in the elastic membrane element to prevent unintentional outflow of the fluid. In which, the plug member has a spherical seal surface with which the elastic membrane element elastically and closely contacts; and at least one thick wall portion and at least one thin wall portion are alternately formed around the discharge opening of the elastic membrane element in a circumferential direction thereof.

By this feature of the invention, when fluid is discharged through the discharge opening, in the elastic membrane element made of an elastic material, the thin wall portion can be swelled and expanded more easily than the thick wall portion, and the fluid is discharged through the discharge opening by way of the thin wall portion due to a rise in internal pressure. At this time, since the thick wall portion is more difficult to be swelled and expanded than the thin wall portion, the thick wall portion restrains the plug member from being moved to the discharge opening to close the discharge opening. Accordingly, when the backflow preventing mouth plug according to the invention is used, the plug member does not close the discharge opening and the fluid can be reliably discharged through the discharge opening. On the other hand, when the backflow preventing mouth plug according to the invention is not used, as the elastic membrane element contacts closely with the plug member, it is possible to prevent a void from being created between the discharge opening and the plug member and the fluid remaining between the plug member and the elastic membrane element.

According to another aspect of the invention, the elastic membrane element has a substantially semi-spherical tip part; the discharge opening is defined through a projecting end of the tip part; the plug member is provided to contact closely with an inner surface of the tip part; and the thick wall portion is provided on the tip part of the elastic membrane element between a position vertically corresponding to a spherical center of the plug member and the discharge opening. By this feature of the invention, since the thick wall portion is formed on the tip part more adjacent to the discharge opening than a position vertically corresponding to a spherical center of the plug member, the thick wall portion reliably restrains the movement of the plug member so that the discharge opening is not closed by the plug member while discharging the fluid through the discharge opening, and a flow path for the fluid can be secured due to the alternate location of the thick wall portion and the thin wall portion.

According to another aspect of the invention, an annular protrusion is formed on an inner surface of the elastic membrane element to contact closely with the plug member to thereby define a seal. By this feature of the invention, due to the accomplishment of a double seal structure that comprises a first seal by a spherical surface of the plug member and a second seal due to close contact between the annular protrusion and the plug member, it is possible to improve a sealing performance of the backflow preventing mouth plug.

According to another aspect of the invention, a plurality of plug members is disposed in the elastic membrane element. By this feature of the invention, it is possible to further improve the sealing performance of the backflow preventing mouth cap.

According to another aspect of the invention, the elastic membrane element has, adjacent to one end thereof, a substantially semi-spherical tip part; the discharge opening is defined through a projecting end of the tip part; the at least one thick wall portion and the at least one thin wall portion are alternately formed on the tip part in a circumferential direction of the tip part; the plug member is composed of a first plug member and a second plug member each having a spherical seal surface with which the elastic membrane element elastically and closely contacts, the first plug member being disposed in the tip part of the elastic membrane element, and the second plug element being disposed more adjacent to the mouth part of the container than the first plug member in the elastic membrane element. By this feature of the invention, it is possible to further improve the sealing performance of the backflow preventing mouth plug by disposing the first and second plug members in the elastic membrane element.

According to another aspect of the invention, the first plug member has a spherical configuration and is disposed to contact closely with an inner surface of the tip part; and the at least one thick wall portion is formed on the tip part of the elastic membrane element between a position vertically corresponding to a spherical center of the first plug member and the discharge opening. By this feature of the invention, since the thick wall portion is formed on the tip part more adjacent to the discharge opening than a position vertically corresponding to a spherical center of the first plug member, the thick wall portion reliably restrains the movement of the first plug member so that the discharge opening is not closed by the first plug member while discharging the fluid through the discharge opening.

According to another aspect of the invention, annular protrusions are formed on an inner surface of the elastic membrane element to contact closely with the first and/or second plug members to thereby define seals. By this feature of the invention, due to the accomplishment of a multi-seal structure which comprises seals by spherical surfaces of the first and second plug members and seals due to close contact between the annular protrusions and the first and/or second plug members, it is possible to still further improve the sealing performance of the backflow preventing mouth plug.

According to another aspect of the invention, the backflow preventing mouth plug further includes a mounting member for mounting the elastic membrane element to the mouth part of a container body of the container, and a restraining part for restraining a position of the second plug member in the elastic membrane element is formed on the mounting member. By this feature of the invention, due to the presence of the restraining part, it is possible to set a position of the second plug member.

According to another aspect of the invention, an annular cover part for covering an upper part of the mounting member is formed on an outer surface of the elastic membrane element. By this feature of the invention, it is possible to prevent foreign substances from entering between the mounting member and the elastic membrane element.

According to still another aspect of the invention, a restraining projection for restraining positions of the first and second plug members is formed on the inner surface of the elastic membrane element. By this feature of the invention, it is possible to set positions of the first and second plug members.

According to yet still another aspect of the invention, at least one thick wall portion and at least one thin wall portion are alternately formed in a circumferential direction of a body part of the elastic membrane element on a middle portion of the body part. By this feature of the invention, it is possible to restrain the movement of the second plug member by the thick wall portion.

According to further still another aspect of the invention, there is provided a container wherein the backflow preventing mouth plug as described above is mounted to a mouth part of a container body. By this feature of the invention, it is possible to prevent the container from being oxidized or contaminated and to use the container for a lengthy period of time.

DESCRIPTION OF THE PREFERRED EMBODIMENT

Figure 1:
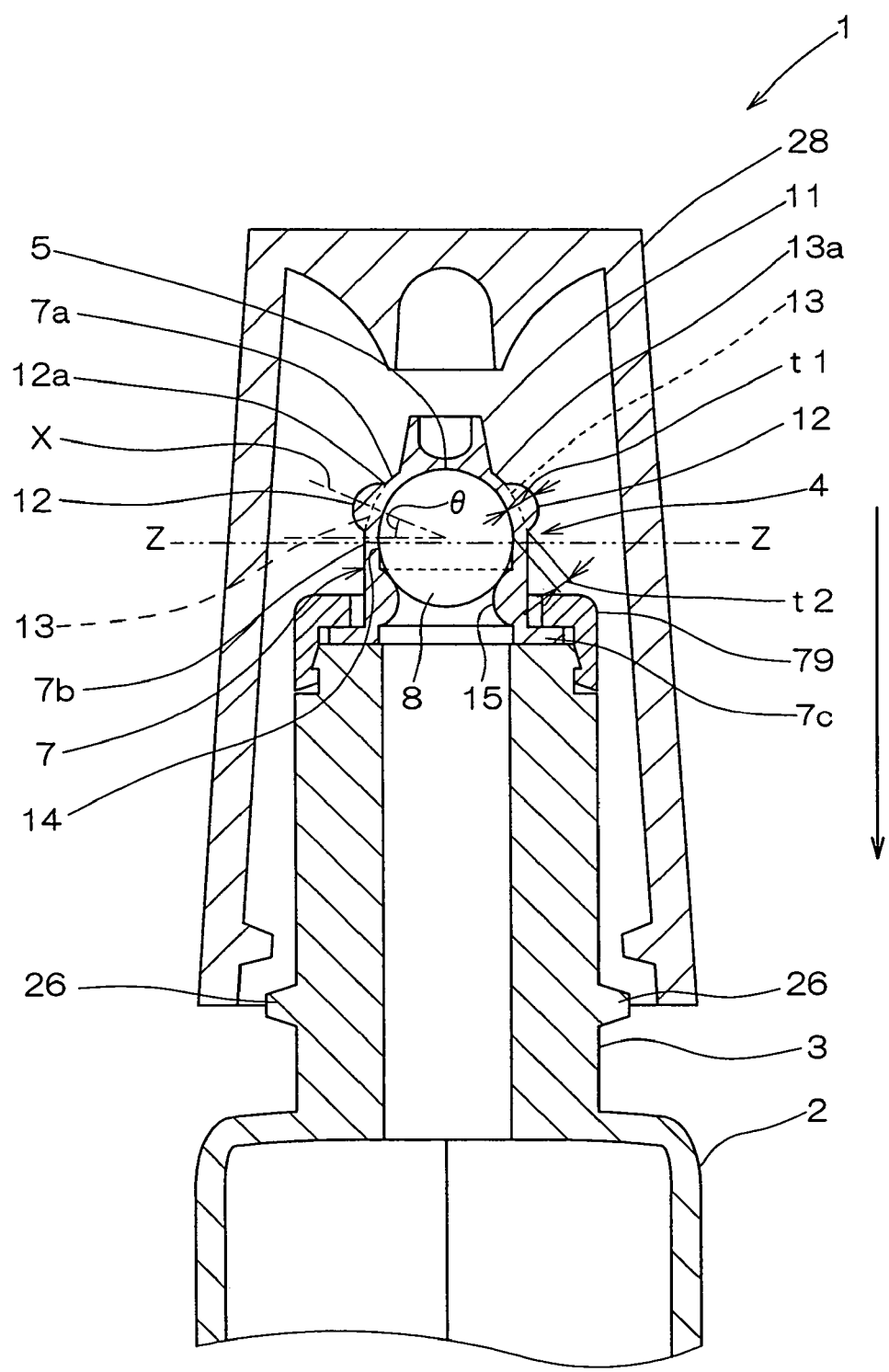
FIG. 1 is a longitudinal sectional view illustrating a container in accordance with a first embodiment of the invention.
Figure 2:
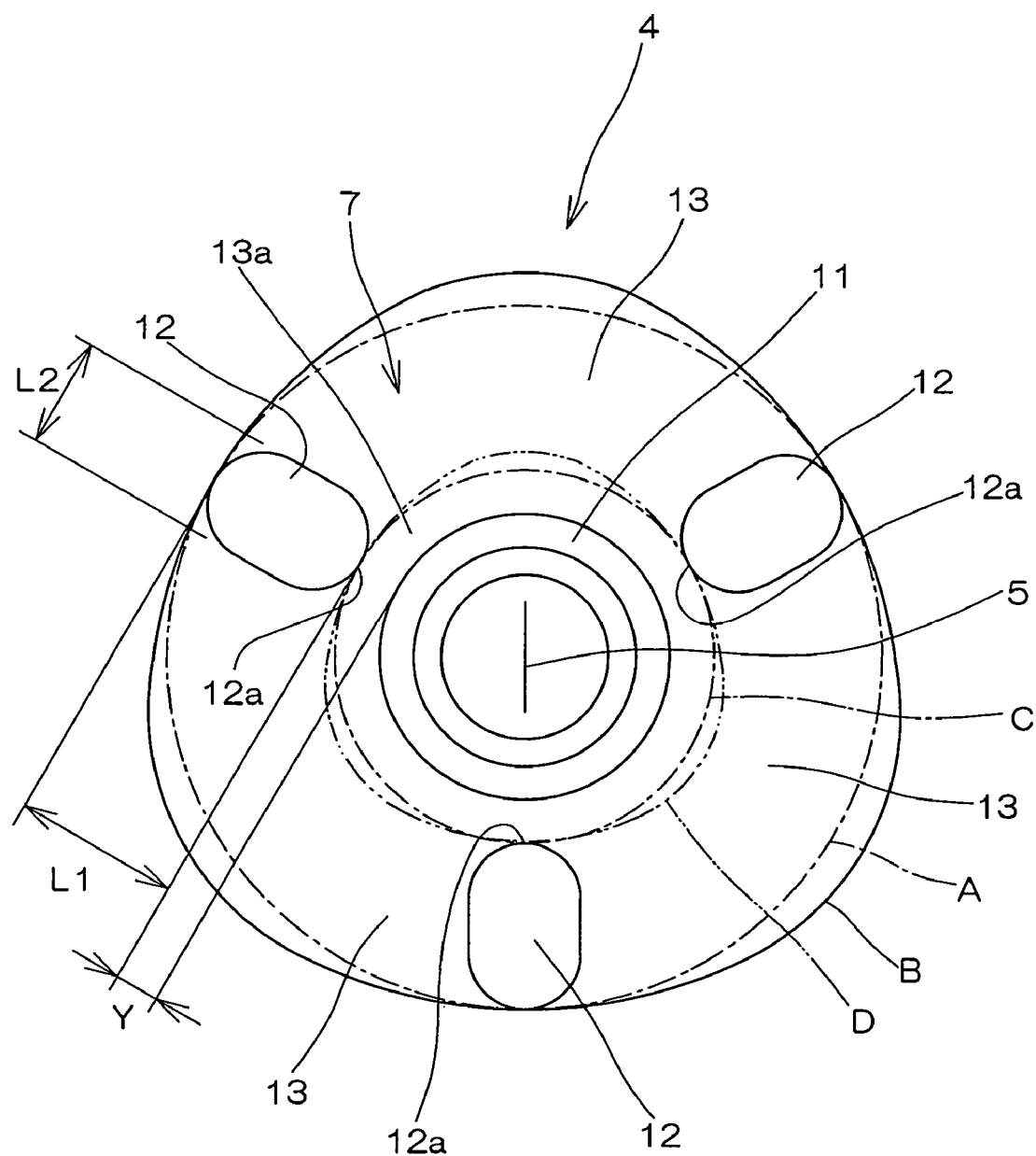
FIG. 2 is a development view taken along the line Z-Z of FIG. 1, illustrating an elastic membrane element.

In a first embodiment of the invention as shown in FIGS. 1 and 2, a container 1 has a container body 2 which is squeezable, and a backflow preventing mouth plug 4 which is provided on a mouth part 3 of the container body 2. The backflow preventing mouth plug 4 is secured to the mouth part 3 by caulking. When in use, the backflow preventing mouth plug 4 can discharge fluid accommodated in the container 1 through a discharge opening 5 defined in a tip part of the mouth plug 4. The fluid accommodated in the container 1 may comprise a substance having flowability, such as liquid, paste, gas, and the like. In the present embodiment, descriptions will be made on the assumption that the fluid comprises an eye lotion (instillation medicine) that can be used by dripping a droplet out of a container 1.

The container body 2 has a bellows-shaped configuration so that an internal pressure rises when the container body 2 is pressed from the outside. A cylindrical mouth part 3 is formed on an upper end of the container body 2.

The backflow preventing mouth plug 4 has an elastic membrane element 7 in which the discharge opening 5 is defined, and a plug member 8 disposed in the elastic membrane element 7 to prevent unintentional outflow of the fluid.

The elastic membrane element 7 is formed of a thin film and is elastically brought into close contact with the plug member 8. The elastic membrane element 7 has a sack-shaped configuration including a tip part 7a formed in a substantially semi-spherical dome shape and a body part (middle part) 7b formed in a cylindrical shape.

The elastic membrane element 7 is formed, at a base part thereof, with circumferential collar part 7c to be secured to the mouth part 3 of the container 1 by a mounting member (caulking member) 79 formed of a suitable material, for example, resin or metal. Therefore, the backflow preventing mouth plug 4 is constructed in a manner such that it can be easily secured to an upper end of the mouth part 3 of the container 1 by the mounting member 79. A radially outwardly projecting protuberance 26 is formed on an outer surface of the mouth part 3, so that a cap 28 can be locked with the protuberance 26 of the mouth part 3.

The discharge opening 5 which is defined through a projecting end of the tip part 7a of the elastic membrane element 7 may have a shape of a slit which is cut in a form of '−' or '+', or in a shape of a duckbill, the edges of the opening 5 being brought into contact with each other. Around the discharge opening 5, the elastic membrane element 7 is formed with a cylindrical portion 11 that projects in a discharge direction of the fluid.

In the case that the fluid comprises liquid such as an eye lotion, the cylindrical portion 11 serves as a liquid storing section for storing a predetermined amount of liquid discharged through the discharge opening 5 by inducing a surface tension on the fluid. In this way, since the predetermined amount of liquid such as an eye lotion is stored in the liquid storing section 11, it is possible to supply a desired amount of droplet. Further, since the liquid storing section 11 is formed to project in the discharge direction of the fluid, it may serve as a reference guide for guiding a precise position to which a droplet is to be dripped to a person's eye.

As can be readily seen from FIGS. 1 and 2, a plurality of (three in this embodiment) thick wall portions 12 are formed on the elastic membrane element 7 below the discharge opening 5. The thick wall portions 12 are formed to be spaced apart one from another in a circumferential direction of the semispherical tip part 7a (or in a circumferential direction of the body part 7b of the elastic membrane element 7). Specifically, the thick wall portions 12 are formed to be uniformly spaced apart one from another around the discharge opening 5. A plurality of thin wall portions 13 which can be swelled and expanded more easily than the thick wall portions 12 are formed between the thick wall portions 12. Accordingly, as shown in FIG. 2, the thick wall portions 12 and the thin wall portions 13 are alternately formed around the discharge opening 5.

The thick wall portions 12 have a shape of a protuberance that is bulged outward from an outer surface of the elastic membrane element 7. As shown in FIG. 2, each thick wall portion 12 is formed to have substantially an elliptical outline in front view. In this first embodiment of the invention, a length L1 of the thick wall portion 12 which is measured in a lengthwise direction thereof (hereinafter, referred to as "vertical direction") is larger than a length L2 of the thick wall portion 12 which is measured in the circumferential direction. A ratio (L1/L2) of the length L1 of the thick wall portion 12 to the length L2 thereof is set to about 2.

Referring to FIG. 1, an outer surface of the thick wall portion 12 has an arc-shaped contour that is bulged outward. Therefore, the thick wall portion 12 has a maximum thickness at a vertical middle position (which corresponds to a position along the one-dot chain line X in FIG. 1), and the thickness of the thick wall portion 12 is gradually decreased toward both vertical ends thereof. The thick wall portions 12 are positioned above a spherical center of the plug member 8. Accordingly, the thick wall portion 12 is formed on the tip part 7a of the elastic membrane element 7 between a position vertically corresponding to the spherical center of the plug member 8 and the discharge opening 5. Specifically, as shown in FIG. 1, the thick wall portion 12 is formed on the elastic membrane element 7 within a range between a position at which a horizontal line (two-dot line Z in FIG. 1) passing through the spherical center of the plug member 8 passes and a base position of the cylindrical portion (liquid storing section) 11.

An angle θ between a line connecting the vertical middle position of the thick wall portion 12 with the center of the plug member 8 and a horizontal line is preferably set in the range of $0° < \theta < 60°$, and more preferably in the range of $10° \leq \theta \leq 30°$.

Further, in the elastic membrane element 7, a ratio (t1/t2) of a maximum thickness t1 of the thick wall portion 12 to a thickness t2 of the thin wall portion 13 is set to about 2, 3 or 4.

In FIG. 2, the character 'Y' designates a distance between an upper end 12a of the thick wall portion 12 adjacent to the discharge opening 5 and a lower end of an outer surface of the cylindrical portion 11. The distance Y serves as a distance for separating the plug member 8 from the discharge opening 5 in a fluid discharge direction when the fluid is discharged through the discharge opening 5. By establishing the distance Y in this way, between the upper end 12a of the thick wall portion 12 and the cylindrical portion 11, there is provided a thin wall portion 13a which is swelled and expanded more easily than the thick wall portions 12. In other words, the thin wall portion 13a is formed around the lower end of the outer surface of the cylindrical portion 11 or around the discharge opening 5 between the upper ends 12a of the thick wall portions 12 and the lower end of the outer surface of the cylindrical portion 11 or the discharge opening 5. By forming the thin wall portion 13a around the lower end of the outer surface of the cylindrical portion 11 or around the discharge opening 5 in this way, the fluid which has passed by the thin wall portions 13 formed between the thick wall portions 12 can be easily guided to the discharge opening 5, whereby smooth flow of the fluid can be ensured.

A material of the elastic membrane element 7 can be freely selected from a group consisting of rubber, resin, and so forth, in consideration of physical characteristics of the fluid, such as a viscosity, a grain size and the like, chemical characteristics of the fluid such as PH and the like, an outer appearance of the elastic membrane element 7, an economic efficiency, convenience in use, etc.

For example, as a material of the elastic membrane element 7, elastic rubber material which is composed of at least one selected from a group consisting of NR, SBR, BR, NBR, CR, EPM, EPDM, IR, IIR, FKM, VMQ, U, T, CO and ACM; SBS, SIBS, SEBS, SIS, SEPS, SEEPS, TPO, TPU, TPEE, TPAE, TPVC, 1,2-polybutadiene-based thermoplastic elastomer; fluoride-based thermoplastic elastomer; and a composite thereof can be used.

The plug member 8 is disposed in the body part 7b of the elastic membrane element 7 and comprises a solid spherical body made of, for example, hard resin. The diameter of the plug member 8 is greater than the inner diameter of the body part 7b of the elastic membrane element 7.

Hence, when the plug member 8 is disposed in the body part 7b of the elastic membrane element 7, the plug member 8 contacts closely with an inner surface of the elastic membrane element 7, so that the body part 7b of the elastic membrane element 7 that is brought into close contact with the plug member 8 is elastically deformed to be expanded outward. The plug member 8 is pressed by an elastic force generated as the elastic membrane element 7 is deformed, to be supported in the elastic membrane element 7.

Since the plug member 8 is a spherical body, its surface provides a spherical surface. The elastic membrane element 7 is elastically brought into close contact with the spherical surface, so that the plug member 8 performs sealing function. Hereinafter, the spherical surface of the plug member 8 which seals in this way will be referred to as a spherical sealing surface 14, and a seal by the spherical sealing surface 14 will be referred to as a first seal. Since the spherical sealing surface 14 has a spherical configuration, a sealing area larger than a flat surface can be obtained.

Since the elastic membrane element 7 is formed of a thin film material, at a region where the elastic membrane element 7 is brought into close contact with the plug member 8, the inner and outer surfaces of the elastic membrane element 7 are elastically deformed in conformity with the spherical configuration of the spherical sealing surface 14. Consequently, at the close contact region, the sealing between the spherical sealing surface 14 and the elastic membrane element 7 is accomplished by the close contact between the spherical surfaces. As the spherical surfaces are brought into close contact with each other, the elastic force of the elastic membrane element 7 at each close contact point acts in a direction toward a spherical center of the spherical sealing surface 14.

Namely, uniform elastic force (elastic returning force) acts at any contact point in the direction toward the spherical center. Due to this fact, close contactability is improved, and a reliable and precise backflow preventing function over a wide area is accomplished.

An annular protrusion (sealing part) 15 is formed on the inner surface of the body part 7b of the elastic membrane element 7, to be brought into contact with the plug member 8 to thereby define a second seal in addition to the first seal defined by the spherical sealing surface 14. As shown in FIG. 1, the annular protrusion 15 has an arc-shaped curved contour in sectional view. The annular protrusion 15 projects inward from the inner surface of the body part 7b of the elastic membrane element 7, and the plug member 8 contacts closely with the annular protrusion 15 along the entire circumference of the annular protrusion 15 for sealing.

In the elastic membrane element 7, a double seal structure including the spherical sealing surface 14 (first seal) and the close contact portion (second seal) between the plug member 8 and the annular protrusion 15 is attained. Therefore, by this double seal structure, the backflow preventing mouth plug 4 can perform a reliable and sufficient backflow preventing function.

Hereafter, a process in which the fluid accommodated in the container 1 is discharged to the outside through the discharge opening 5 will be described.

When an inner pressure rises by pressing the squeezable container body 2 from the outside, the fluid presses the plug member 8 toward the discharge opening 5. At this time, the plug member 8 is detached from the annular protrusion 15 to release the second seal. Then, the fluid forcibly extends the elastic membrane element 7 excluding the thick wall portions 12, so that the elastic membrane element 7 excluding the thick wall portions 12 is detached from the spherical sealing surface 14. Thus, the first seal is released, and the fluid is discharged through the discharge opening 5 after passing between the spherical sealing surface 14 and the thin wall portions 13.

At this time, the thin wall portions 13 are expanded from a position shown by the one-dot chain line A to a position shown by the solid line B in FIG. 2. Also, the thin wall portion 13 which is placed in an imaginary circle defined by the upper ends of the thick wall portions 12 is expanded and deformed from a position shown by the one-dot chain line C to a position shown by the two-dot chain line D. Thus, a flow path which extends to the discharge opening 5 is created between the thin wall portions 13 and the spherical sealing surface 14, and the fluid is discharged to the outside through the discharge opening 5 after passing through the flow path.

As described above, as the fluid passes by the thin wall portions 13, the plug member 8 is pressed by the fluid to move toward the discharge opening 5. However, due to the fact that the thick wall portions 12 are less swellable and expandable than the thin wall portions 13, the plug member 8 is restrained from being moved toward the discharge opening 5 under the influence of the thick wall portions 12, whereby the plug member 8 is not allowed to close the inner side of the discharge opening 5 defined through the elastic membrane element 7 and thereby it is possible to reliably secure the flow path of the fluid.

As a consequence, due to the thick wall portions 12 formed on the elastic membrane element 7, the plug member 8 is prevented from closing the discharge opening 5 when the fluid is discharged through the discharge opening 5, while the plug member 8 and the elastic membrane element 7 are brought into close contact with each other to close and seal the discharge opening 5 from the inside when the fluid is not discharged through the discharge opening 5. Specifically, by causing a region of the elastic membrane element 7 extending from the body part 7b to the tip part 7a thereof to be brought into close contact with the plug member 8, it is possible to prevent a void from being created between the plug member 8 and the discharge opening 5 and the fluid from remaining between the plug member 8 and the discharge opening 5. Thus, the fluid accommodated in the container 1 can be stored for an extended period of time without being oxidized or contaminated.

In addition, since the plug member 8 can be brought into close contact with the region of the elastic membrane element 7 extending from the body part 7b to the dome-shaped tip part 7a thereof, it is possible to secure a larger sealing area (corresponding to at least a half of a surface area of the plug member 8), whereby a sealing function can be improved.

Figure 3:
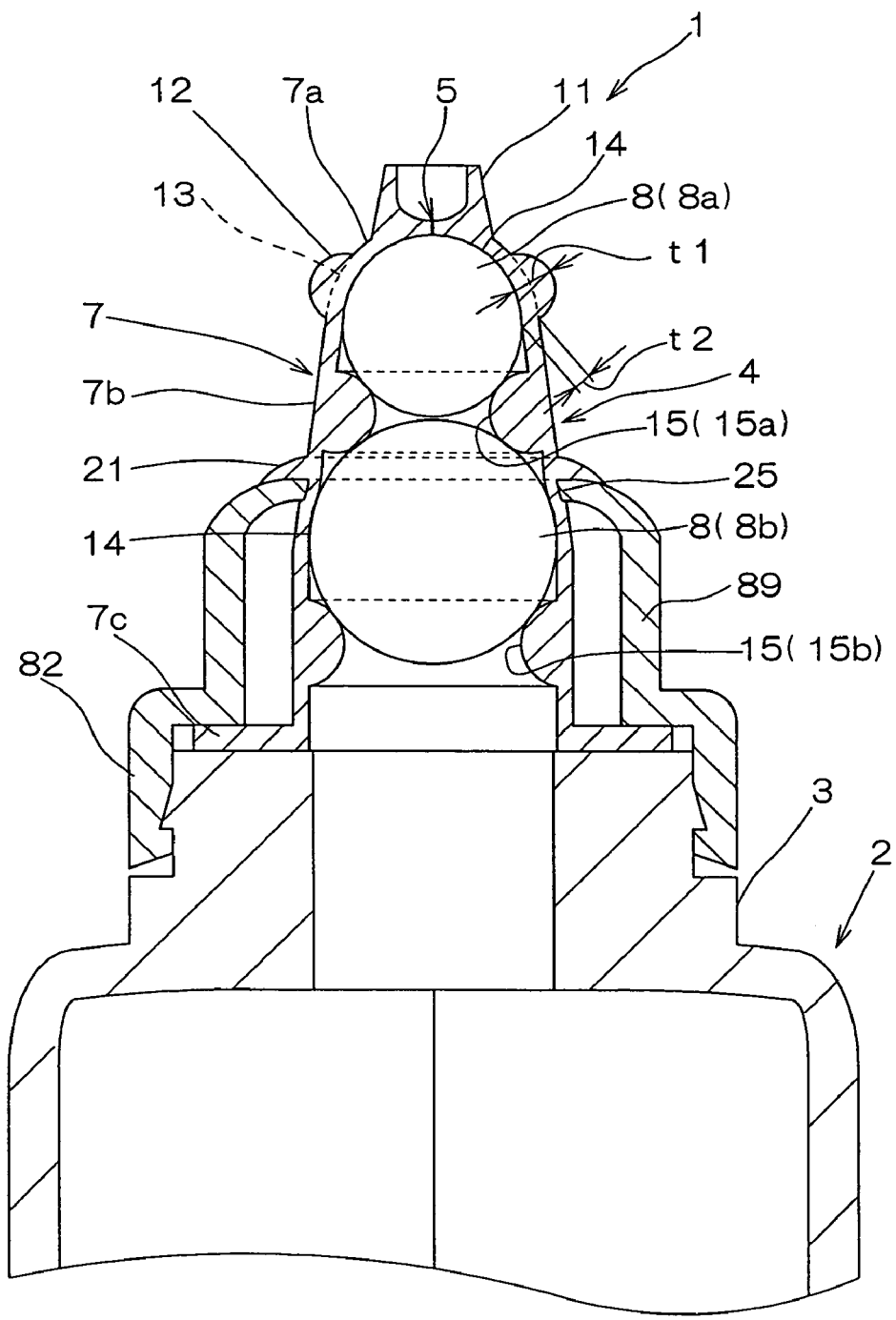
FIG. 3 is a longitudinal sectional view illustrating a container in accordance with a second embodiment of the invention.
Figure 4:
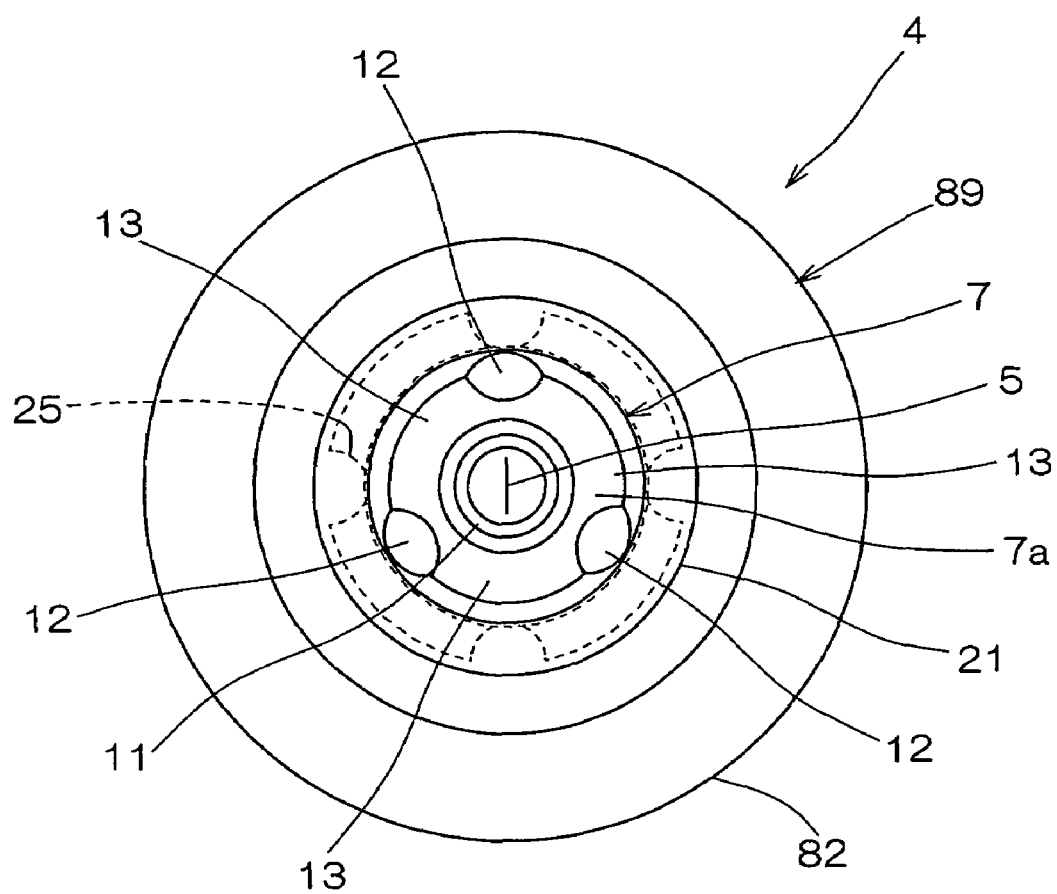
FIG. 4 is a plan view illustrating the container according to the second embodiment of the invention.

In a second embodiment of the invention as shown in FIGS. 3 and 4, an annular cover part 21 for covering an upper part of a mounting member 89 is formed on the outer surface of the elastic membrane element 7. As the annular cover part 21 covers the upper part of the mounting member 89, it is possible to prevent a gap from being created between the elastic membrane element 7 and the mounting member 89, whereby design-related advantages are obtained and foreign substances are prevented from being entered between the elastic membrane element 7 and the mounting member 89.

A pair of plug members 8 (8a and 8b) is disposed in the elastic membrane element 7. The first plug member 8a is disposed to contact closely with the inner surface of the tip part 7a of the elastic membrane element 7, and the second plug member 8b is disposed adjacent to the mouth part 3 of the container body 2 in the body part 7b of the elastic membrane element 7.

The diameter of the second plug member 8b is greater than that of the first plug member 8a, so that the second plug member 8b deforms the elastic membrane element 7 to a greater extent than the first plug member 8a to increase a sealing degree. In the backflow preventing mouth plug 4 according to this second embodiment, by differentiating the diameters of the first and second plug members 8a and 8b in this way, it is possible to partially intensify or adjust a sealing force.

The diameter of the second plug member 8b is made slightly larger than the inner diameter of the mouth part 3, so that the second plug member 8b is prevented from being fitted into the mouth part 3. Therefore, since the inner diameter of the mouth part 3 may be determined corresponding to the diameter of the second plug member 8b, the inner diameter of the mouth part 3 can be increased by increasing the diameter of the second plug member 8b, whereby filling of the container body 3 with the fluid is facilitated.

Although the first plug member 8a is formed to have a diameter less than that of the second plug member 8b, since the second plug member 8b is positioned between the first plug member 8a and the mouth part 3, the first plug member 8a is prevented from being inserted into the mouth part 3.

As shown in FIG. 3, annular protrusions (sealing parts) 15 are formed on the inner surface of the elastic membrane element 7 so as to be brought into close contact with the first and second plug members 8 (8a and 8b) to perform sealing functions. The annular protrusions 15 comprise a first annular protrusion 15a that is to be brought into contact with the first plug member 8a, and a second annular protrusion 15b that is to be brought into contact with the second plug member 8b. The first and second annular protrusions 15a and 15b have an arc-shaped contour in their cross-sections. The annular protrusions 15 (15a and 15b) project inward from the inner surface of the body part 7b of the elastic membrane element 7. As the plug members 8 (8a and 8b) contact closely with the entire circumferences of the annular protrusions 15 (15a and 15b), sealing is effected.

An upper portion of the first annular protrusion 15a is brought into contact with a lower portion of the first plug member 8a to perform a sealing function and restrains a position of the first plug member 8a. A lower portion of the first annular protrusion 15a is brought into close contact with an upper portion of the second plug member 8b to perform a sealing function.

The second annular protrusion 15b is brought into contact with a lower portion of the second plug member 8b to perform a sealing function and restrains a position of the second plug member 8b. The second plug member 8b is sandwiched between the first and second annular protrusions 15a and 15b for sealing.

Therefore, the backflow preventing mouth plug 4 according to this second embodiment has a multi-seal structure comprising the close contact portions between the plug members 8 (8a and 8b) and the inner surface of the elastic membrane element 7 and the close contact portions between the plug members 8 (8a and 8b) and the annular protrusions 15 (15a and 15b), whereby the backflow preventing mouth plug 4 can perform a reliable and sufficient backflow preventing function.

The mounting member 89 has a cylindrical configuration including at a lower end thereof a mounting part 82 for mounting the elastic membrane element 7 to the mouth part 3. The mounting part 82 captures the annular collar part 7c of the elastic membrane element 7 against the upper end of the mouth part 3 for securing the elastic membrane element 7 to the mouth part 3 of the container body 2.

A restraining part 25 for restraining a position of the second plug member 8b in the elastic membrane element 7 is formed at an upper end of the mounting member 89. The restraining part 25 comprises a plurality of (four in this embodiment) restraining projections that project inward from the upper end of the mounting member 89 (hereinafter, the restraining part and the restraining projections are referred by the same reference numeral 25). The restraining projections 25 are uniformly spaced apart one from another at the upper end of the mounting member 89 in a circumferential direction thereof.

The restraining projections 25 abut the outer surface of the elastic membrane element 7 and restrain the position of the second plug member 8b through the elastic membrane element 7.

Hereafter, a process in which the fluid accommodated in the container 1 is discharged through the discharge opening 5 to the outside according to this second embodiment of the invention will be described.

When an inner pressure rises by pressing the squeezable container body 2 from the outside, the fluid biases the second plug member 8b toward the discharge opening 5.

At this time, the second plug member 8b is detached from the second annular protrusion 15b to release the seal by the second annular protrusion 15b. Although the second plug member 8b is pressed by the fluid toward the first plug member 8a, since the second plug member 8b is restrained from being moved toward the first plug member 8a by the restraining part 25 of the mounting member 89, a portion of the body part 7b of the elastic membrane element 7 which is closer to the tip part 7a than the restraining part 25 is expanded, so that the fluid releases the seal between the spherical sealing surface 14 of the second plug member 8b and the inner surface of the elastic membrane element 7, the seal between the second plug member 8b and the first annular protrusion 15a, and the seal between the first plug member 8a and the first annular protrusion 15a, and then finally flows into the tip part 7a of the elastic membrane element 7.

The fluid flowing into the tip part 7a of the elastic membrane element 7 passes by the elastic membrane element 7 excluding the thick wall portions 12 for restraining the movement of the first plug member 8a with releasing the seal between the spherical sealing surface 14 of the first plug member 8a and the inner surface of the elastic membrane element 7, whereby the fluid is discharged through the discharge opening 5 after passing between the spherical sealing surface 14 and the thin wall portions 13.

At this time, the thin wall portions 13 are expanded as shown in FIG. 2 from the first embodiment, so that a flow path which extends to the discharge opening 5 is created between the thin wall portions 13 and the spherical sealing surface 14, and the fluid is discharged to the outside through the discharge opening 5 after passing through the flow path. Except the above features, the second embodiment is constructed in the same manner as the first embodiment and achieves the same working effects as the first embodiment. Accordingly, in this second embodiment, the same reference numerals were used to refer to the same or like parts (This is applied to the following third to fifth embodiments of the invention).

Figure 5:
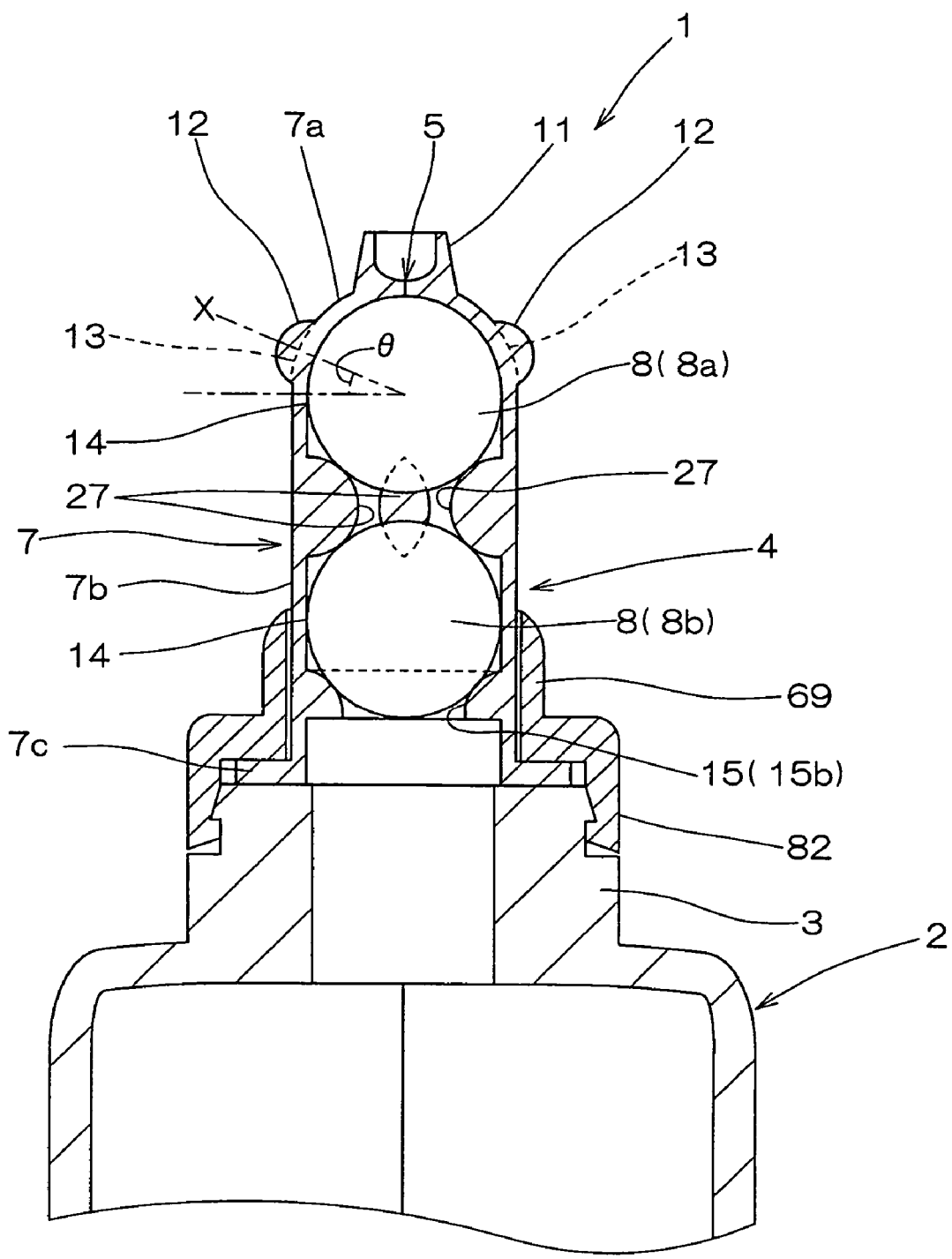
FIG. 5 is a longitudinal sectional view illustrating a container in accordance with a third embodiment of the invention.

A third embodiment as shown in FIG. 5 is differentiated from the second embodiment in that the first annular protrusion 15a of the second embodiment is not formed on the inner surface of the elastic membrane element 7, a restraining part 27 for restraining positions of the plug members 8 (8a and 8b) is formed on the inner surface of the elastic membrane element 7, and the restraining part 25 of the second embodiment is not formed on the mounting member 69.

The restraining part 27 which is formed on the inner surface of the elastic membrane element 7 comprises a plurality of (four in this embodiment) restraining projections which project inward from the inner surface of the elastic membrane element 7 (hereinafter, the restraining part and the restraining projections of the elastic membrane element 7 are referred by the same reference numeral 27). The restraining projections 27 are uniformly spaced apart one from another on the inner surface of the elastic membrane element 7 in a circumferential direction thereof. Except the above features, the third embodiment is constructed in the same manner as the second embodiment and achieves the same working effects as the second embodiment.

Figure 6:
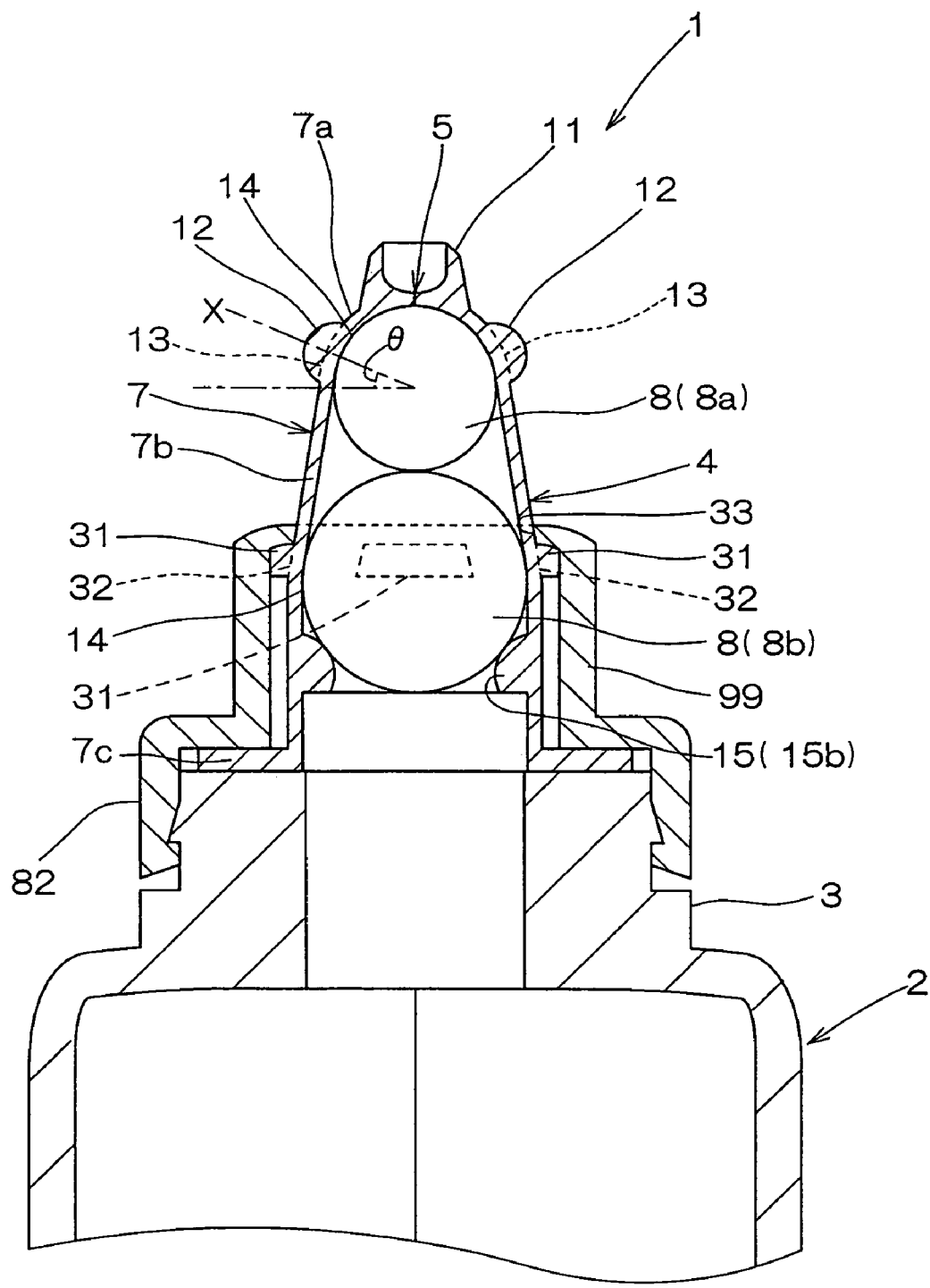
FIG. 6 is a longitudinal sectional view illustrating a container in accordance with a fourth embodiment of the invention.
Figure 7:
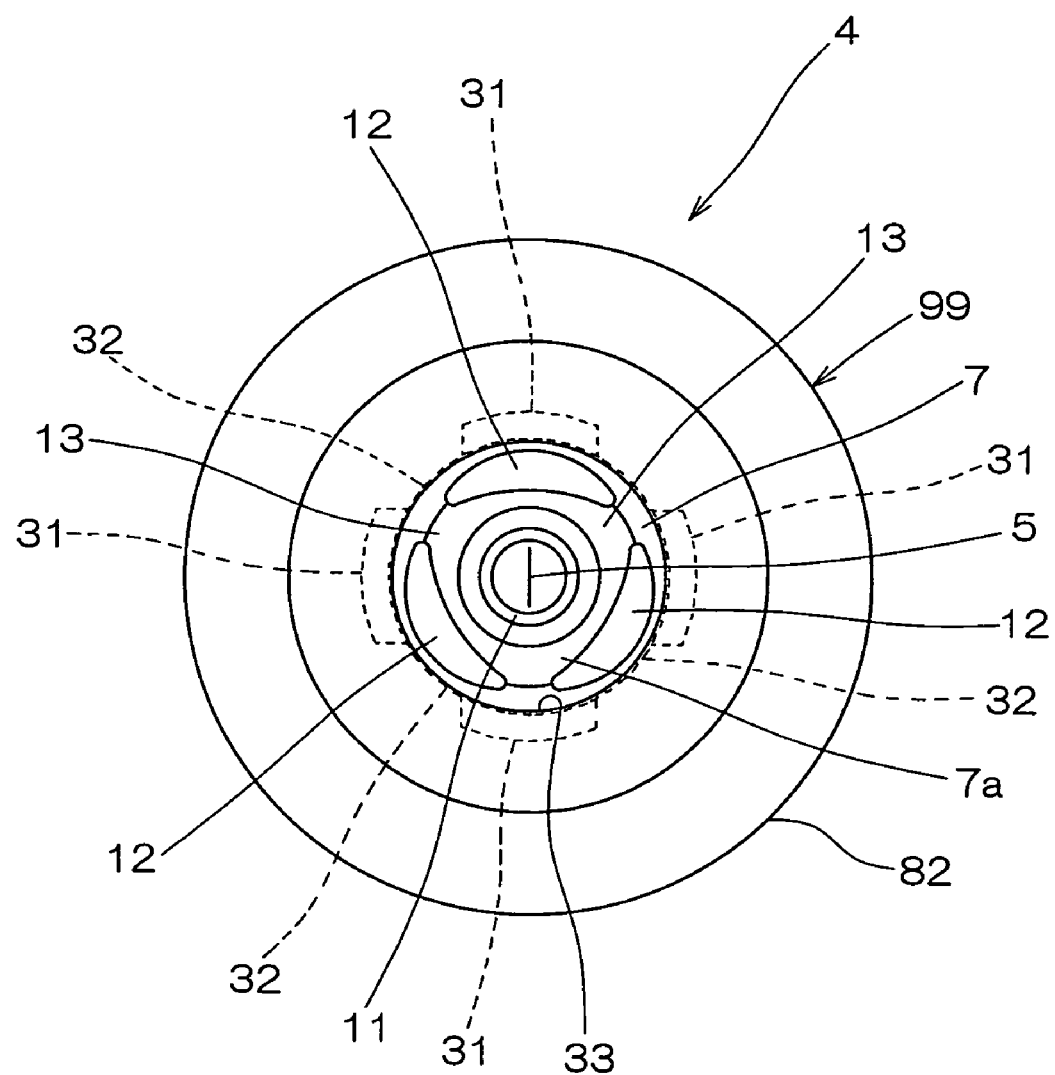
FIG. 7 is a plan view illustrating the container according to the fourth embodiment of the invention.

A fourth embodiment of the invention as shown in FIGS. 6 and 7 is differentiated from the second embodiment in that thick wall portions 31 and thin wall portions 32 which act on the second plug member 8b are formed on the elastic membrane element 7, the first annular protrusion 15a of the second embodiment is not formed, and a mounting member 99 has a different configuration.

In this fourth embodiment, a length L2 of the thick wall portion 12 which is measured in the circumferential direction is larger than a length L1 of the thick wall portion 12 which is measured in the vertical direction. A ratio (L1/L2) of the length L1 of the thick wall portion 12 to the length L2 thereof is set to less than 1. Further, the ratio of the length L2 of the thick wall portion 12 to a circumferential length of each thin wall portion 13, namely, an interval between each pair of adjoining thick wall portions 12, is set to 3:1 or 4:1.

While the thick wall portions 12 and the thin wall portions 13 are formed on the tip part 7a of the elastic membrane element 7 to restrain the first plug member 8a in the second embodiment, the plurality of (respectively four in the figure) thick wall portions 31 and thin wall portions 32 may be alternately formed on the middle portion of the body part 7b of the elastic membrane element 7 in the circumferential direction thereof to restrain a position of the second plug member 8b as in this fourth embodiment.

The restraining projections 25 of the second embodiment are not formed at the upper part of the mounting member 99. As can be readily seen from FIG. 6, the upper part of the mounting member 99 is tapered, so that an inner edge defining a mouth part 33 of the mounting member 99 covers the entire circumference of the middle portion of the elastic membrane element 7, whereby foreign substances are prevented from entering between the elastic membrane element 7 and the mounting member 99. As shown in FIG. 6, the thick wall portions 31 abut the edge of the mouth part 33 of the mounting member 99. Except the above features, the fourth embodiment is constructed in the same manner as the second embodiment and achieves the same working effects as the second embodiment.

Figure 8:
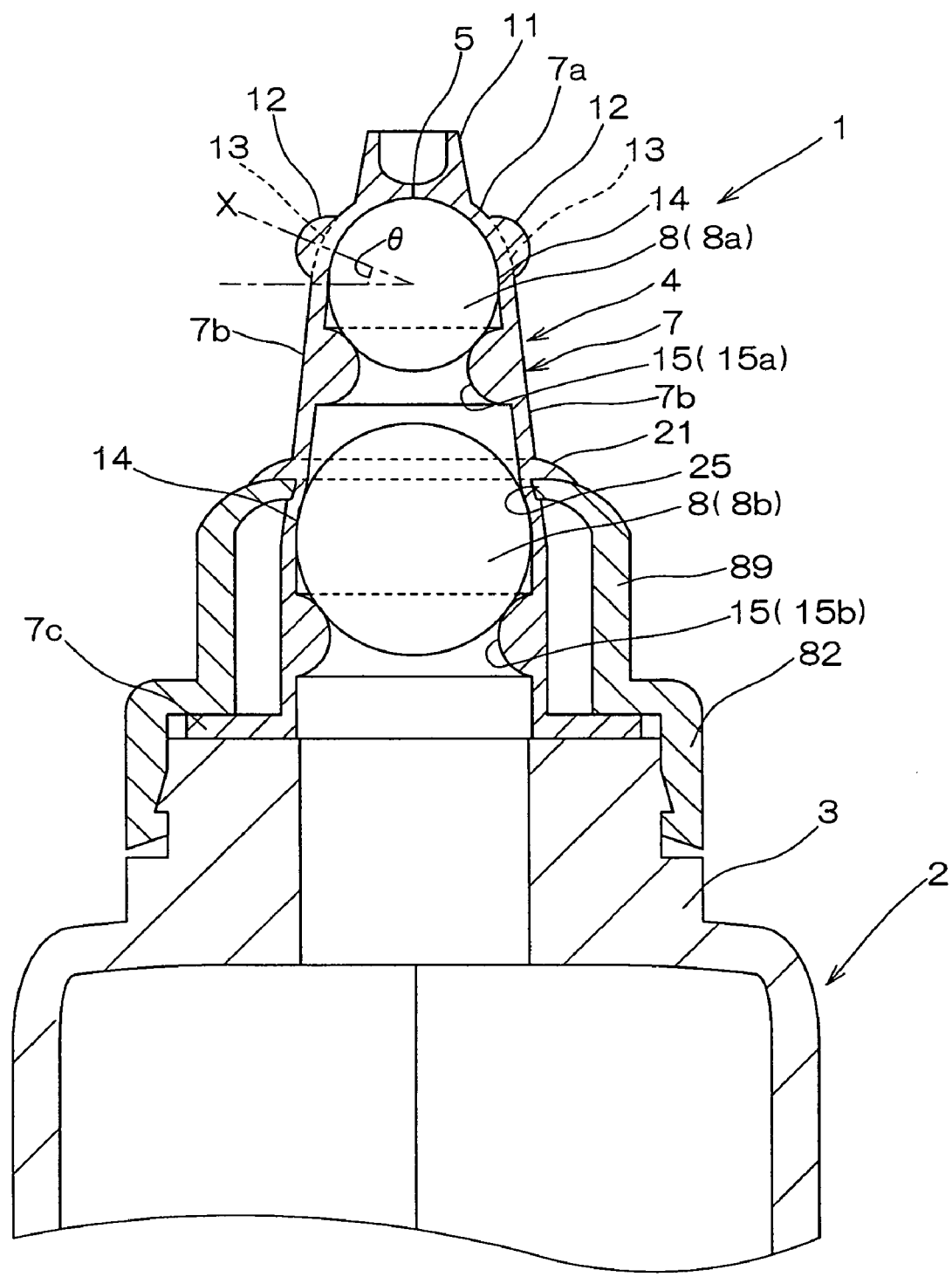
FIG. 8 is a longitudinal sectional view illustrating a container in accordance with a fifth embodiment of the invention.

A fifth embodiment of the invention as shown in FIG. 8 is differentiated from the second embodiment in that the second plug member 8b and the first annular protrusion 15a are not brought into contact with each other. Since the second plug member 8b may be disposed at a separated position from the first annular protrusion 15a, the fifth embodiment is applicable when the elastic membrane element 7 is required to have a substantial length. Except the above feature, the fifth embodiment is constructed in the same manner as the second embodiment and achieves the same working effects as the second embodiment.

It should be noted that the invention is not limited to the above described embodiments, and various changes and modifications can be made as explained below.

That is to say, the number of the thick wall portions 12 may be 1, 2 or greater than 4. The ratio t1/t2 of the maximum thickness t1 of the thick wall portion 12 to the thickness t2 of the thin wall portion 13 may be 2 or greater than 4 in accordance with properties of material of the elastic membrane element 7. The ratio L1/L2 of the length L1 in the vertical direction of the thick wall portion 12 to the length L2 thereof in the circumferential direction may be 3 or greater than 3. Alternatively, the ration L1/L2 may be set to L1≦L2, i.e., 1 or less than 1 so that the area of the thin wall portion 13a (the distance Y) may be increased in the vertical direction.

The liquid storing section 11 that is formed around the discharge opening 5 of the elastic membrane element 7 may be formed to have a prismatic configuration other than the cylindrical configuration. The thick wall portions 12 uniformly spaced apart around the dome-shaped tip part 7a in the circumferential direction thereof in the above embodiments may be non-uniformly spaced apart one from another. Further, the outer surface of the thick wall portions 12 may be formed to have contours other than the arc-shaped contour, and in this case, it was found from experiment results that it is preferable to set an angle θ between a line connecting an apex at the maximum thickness of the thick wall portion 12 with the center of the plug member 8 and a horizontal line, to about 45°, in view of a relationship between the thick wall portions 12 and the thin wall portion 13a (the distance Y).

A plurality of discharge openings 5 may be defined through the elastic membrane element 7, and the shape of the discharge opening 5 is not limited to the duckbill shape, and instead, may have the shape of a circular hole. Moreover, although the discharge opening 5 is defined through the projecting end of the dome-shaped tip part 7a in the above embodiments, the position of the discharge opening 5 may be deviated from the projecting end. Furthermore, the shape of the plug member 8 is not limited to the spherical shape, and instead, may be a shape of a rugby ball, an ellipsoid or the like shape capable of providing a rounded sealing surface. As a material for the plug member 8, metal such as silver or titanium can be used to provide antibacterial properties. These metallic materials may be plated or deposited on the plug member 8 or mixed with resin in a powdered state.

Although the plug member 8 (8a and 8b) comprises two plug members according to the above second to fifth embodiments, at least one spherical plug member 8 may be additionally disposed between the first and second plug members 8a and 8b to provide three or more plug members. In this case, a sealing structure may be accomplished only by close contact between the spherical sealing surface 14 of the plurality of plug members 8 and the elastic membrane element 7 without the annular protrusions 15 (15a and 15b) formed on the inner surface of the elastic membrane element 7. Further, the adjustment for partially intensifying or weakening the seal may be obtained through proper selection of the elongation and hardness of the elastic membrane element 7.

The elastic membrane element 7 may be formed with both of the annular cover part 21 as described in the second embodiment and the thick wall portions 31 as described in the fourth embodiment.

What is claimed is:

1. A backflow preventing mouth plug comprising:
an elastic membrane element having a discharge opening for discharging fluid and mounted to a mouth part of a container and
a plug member disposed in the elastic membrane element to prevent unintentional outflow of the fluid,
wherein the plug member has a spherical seal surface with which the elastic membrane element elastically and closely contacts,
wherein the elastic membrane element has an inner surface in close contact with the spherical seal surface of the plug member, and an opposite outer surface facing away from the spherical seal surface of the plug member,
wherein the discharge opening is located at a projection end of a tip part of the elastic membrane element,
wherein a plurality of thick wall portions and a plurality of thin wall portions are alternately formed after each other and around the discharge opening of the elastic membrane element in a circumferential direction thereof, and
wherein each of the plurality of thick wall portions has a shape of a protuberance that is bulged outward from the outer surface of the elastic membrane element, and is formed closer to the discharge opening than a spherical center of the plug member.

2. The backflow preventing mouth plug according to claim 1, wherein the elastic membrane element has a substantially semi-spherical tip part; the discharge opening is defined through a projecting end of the tip part; the plug member is provided to contact closely with an inner surface of the tip part; and the thick wall portion is provided on the tip part of the elastic membrane element between a position vertically corresponding to a spherical center of the plug member and the discharge opening.

3. The backflow preventing mouth plug according to claim 1, wherein an annular protrusion is formed on an inner surface of the elastic membrane element to contact closely with the plug member to thereby provide a seal.

4. The backflow preventing mouth plug according to claim 2, wherein an annular protrusion is formed on an inner surface of the elastic membrane element to contact closely with the plug member to thereby provide a seal.

5. The backflow preventing mouth plug according to claim 1, wherein a plurality of plug members are disposed in the elastic membrane element.

6. The backflow preventing mouth plug according to claim 1, wherein the elastic membrane element has, adjacent to one end thereof, a substantially semi-spherical tip part; the discharge opening is defined through a projecting end of the tip part; the at least one thick wall portion and the at least one thin wall portion are alternately formed on the tip part in a circumferential direction of the tip part; the plug member comprises a first plug member and a second plug member each having a spherical seal surface with which the elastic membrane element elastically and closely contacts, the first plug member being disposed in the tip part of the elastic membrane element, and the second plug element being disposed more adjacent to the mouth part of the container than the first plug member in the elastic membrane element.

7. The backflow preventing mouth plug according to claim 6, wherein the first plug member has a spherical configuration and is disposed to contact closely with an inner surface of the tip part; and the at least one thick wall portion is formed on the tip part of the elastic membrane element between a position vertically corresponding to a spherical center of the first plug member and the discharge opening.

8. The backflow preventing mouth plug according to claim 6, wherein annular protrusions are formed on an inner surface of the elastic membrane element to contact closely with the first or second plug members to thereby define seals.

9. The backflow preventing mouth plug according to claim 6, wherein the backflow preventing mouth plug further includes a mounting member for mounting the elastic membrane element to the mouth part of a container body of the container; and a restraining part for restraining a position of the second plug member in the elastic membrane element is formed on the mounting member.

10. The backflow preventing mouth plug according to claim 6, wherein the backflow preventing mouth plug further includes a mounting member for mounting the elastic membrane element to the mouth part of a container body of the container; and an annular cover part for covering an upper part of the mounting member is formed on an outer surface of the elastic membrane element.

11. The backflow preventing mouth plug according to claim 6, wherein a restraining projection for restraining positions of the first and second plug members is formed on the inner surface of the elastic membrane element.

12. The backflow preventing mouth plug according to claim 6, wherein at least one thick wall portion and at least one thin wall portion are alternately formed on a middle portion of a body part of the elastic membrane element in a circumferential direction thereof.

13. A container wherein the backflow preventing mouth plug according to claim 1 is mounted to a mouth part of a container body.

14. A container wherein the backflow preventing mouth plug according to claim 2 is mounted to a mouth part of a container body.

15. A container wherein the backflow preventing mouth plug according to claim 6 is mounted to a mouth part of a container body.

* * * * *